United States Patent [19]

Finger

[11] Patent Number: Plant 6,649

[45] Date of Patent: Mar. 7, 1989

[54] KALANCHOE PLANT NAMED HARMONY

[75] Inventor: Herman Finger, Wiesmoor, Fed. Rep. of Germany

[73] Assignee: Wiesmoor-Gartnerie und Baumschule GmbH, Wiesmoor, Fed. Rep. of Germany

[21] Appl. No.: 108,984

[22] Filed: Oct. 16, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Kalanchoe plant named Harmony, having salmon rose flowers, deeply lobed, dark green leaves; vigorous, compact, upright growth; and its very floriferous habit, with flower clusters being positioned above leaves on strong main stems and peduncles.

1 Drawing Sheet

The present invention relates to a new and distinctive cultivar of Kalanchoe plant, botanically known as *Kalanchoe blossfeldiana*, and known by the cultivar name Harmony. Harmony was discovered by me in Wiesmoor, Federal Republic of Germany as a mutation of Seraya (U.S. Plant Pat. No. 5,362). Harmony was discovered growing in a cultivated bed of plants of the parent cultivar, and was recognized by its distinctly different flower color.

Asexual reproduction by me of Harmony in Wiesmoor, Federal Republic of Germany by stem cuttings has shown that the unique features of this new Kalanchoe are stabilized and are reproduced true to type in successive propagations.

The following characteristics distinguish the new Kalanchoe from both its parent varieties and other cultivated Kalanchoes of this type known and used in the floriculture industry:

1. Harmony is characterized by its salmon rose flowers, compared to the salmon pink flowers of Seraya. Cherry Jubilee (U.S. Plant Pat. No. 5,877), Singapur (U.S. Plant Pat. No. 5,361) and Royalty (U.S. Plant Pat. No. 5,254) are more rose red in color. Citation (U.S. Plant Pat. No. 5,533) has a pink flower.

2. Flower size of Harmony is the same as Seraya and Cherry Jubilee but larger than Singapur, Royalty, and Citation.

3. Harmony is not as comapct as Caprice (a cultivar disclosed in my pending application), and is similar in height to Seraya and Cherry Jubilee. Royalty, Singapur and Citation are all taller.

4. Harmony has basal branching similar to Seraya, Royalty, Citation and Singapur, with Cherry Jubilee having better branching.

5. Leaves of Harmony are deeply lobed like Seraya, with all the other comparison cultivars having shallow crenate cutting of the leaf margin.

6. Harmony is similar in maturity to Seraya, Royalty and Citation, with Singapur and Cherry Jubilee being approximately 1 week earlier.

7. Leaves are dark green like Seraya, with all other comparisons having a lighter more yellow-green leaf.

8. Leaves of all comparison cultivars are similar in size to Harmony except Cherry Jubilee which has a slightly smaller leaf.

9. The main stem, peduncles and pedicels of Harmony are similar to Seraya and larger in diameter than Cherry Jubilee, Royalty, Citation and Singapur, thus allowing the plant to hold up its flowers very well.

The accompanying colored photograph illustrates in perspective view the overall appearance of Harmony, with the colors being as true as it is reasonably possible to obtain in a colored reproduction of this type.

The following is a detailed description of my new Kalanchoe variety based on plants produced under commercial practices in Wiesmoor, Federal Republic of Germany and Ashtabula, Ohio. Color references are made to The Royal Horticultural Society Colour Chart, except where general colors of ordinary dictionary significance are used.

Parentage: Mutation of the cultivar Seraya, disclosed in U.S. Plant Pat. No. 5,362.

Propagation:

(A) *Type cutting.*—2 cm long stem cutting.

(B) *Time to root.*—10 days at 21° C. summer. 14 days at 21° C. winter.

(C) *Rooting habit.*—Abundant, fine, fibrous roots.

Plant Description:

(A) *Form.*—Compact, upright, growth; basal branching is average as not every node develops a side branch. Flowers are above foliage and on upper half of plant. Growing and scheduling practices can produce a small plant in a 10 cm pot or a larger plant in a 12 cm pot.

(B) *Habit of growth.*—Vigorous grower with shoots developing from about 60% of the nodes. Internodes are short, thereby producing a compact plant. Bottom of plant is somewhat open but flower cluster is full.

(C) *Foliage.*—Leaves opposite, simple. (1) Size: A full grown leaf of a flowering plant in a 10 cm pot is 95 mm long and 70 mm wide. (2) Shape: Oblong to ovate, apex obtuse, base acute. (3) Texture: Glabrous, succulent, coriaceous. (4) Margin: Pronounced crenate. (5) Color: Young foliage, top side 147A, under side 147B. Mature foliage, top side 148A, under side 148B.

Flowering description:

(A) *Flowering habits.*—Inflorescence is a cyme with the terminal flower of the main axis opening first, followed by terminal flowers of the side branches and then continuing with subsequent development of branches in the inflorescence.

(B) *Natural flowering season.*—Early January. Flowering time under controlled daylength at 20° C. in summer is 11 weeks; in winter 13 weeks. Flowering time depends on temperature, light intensity and other growing conditions.

(C) *Flower buds.*—Elliptical to oblong, up to 8 mm long, developing to tubular as flower petals mature, sheathed with four green sepals. Corolla at maturity 5 mm long.

(D) *Flowers borne.*—Compound dichasial cyme with primary peduncle 4 mm in diameter. Peduncle length depends on growing conditions and B-9 application. Pedicles are up to 8 mm long.

(E) *Quantity of flowers.*—Very floriferous, with more than 250 flowers as both main axis and lateral branches have high numbers of flowers.

(F) *Petals.*—(1) Shape: Almost round, top cuspidate. (2) Color: Top side, when opening, 43B, fading to 50A; under side 39D to 52C. (3) Number of petals: 4.

(G) *Reproductive organs.*—(1) Stamens: Eight (8) in number. (a) Anther shape: Flat, elliptical, color yellow. (b) Filament color: Yellow. (c) Pollen color: Yellow. (2) Pistils. (a) Stigma shape: Flat, color whitish green. (b) Style color: Light green. (c) Ovaries: 4 in number, size 4 mm, color green.

Disease resistance: No disease observed to date.

I claim:

1. A new and distinct cultivar of Kalanchoe plant named Harmony, as illustrated and described.

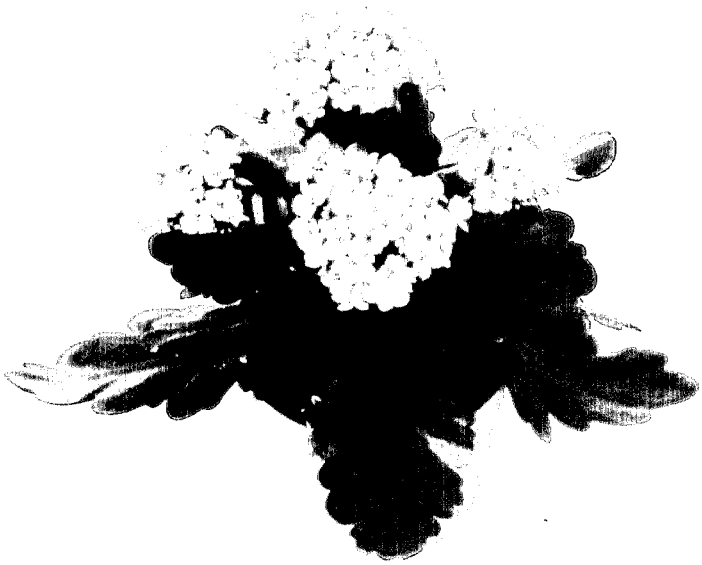

* * * * *